(12) United States Patent
Yanase et al.

(10) Patent No.: US 9,086,321 B2
(45) Date of Patent: Jul. 21, 2015

(54) METHOD OF ANALYZING NITRIDE SEMICONDUCTOR LAYER AND METHOD OF MANUFACTURING NITRIDE SEMICONDUCTOR SUBSTRATE USING THE ANALYSIS METHOD

(71) Applicant: Covalent Materials Corporation, Shinagawa-ku (JP)

(72) Inventors: Yoshihata Yanase, Hadano (JP); Hiroshi Shirai, Hadano (JP); Jun Komiyama, Hadano (JP); Hiroshi Oishi, Hadano (JP)

(73) Assignee: COVALENT MATERIALS CORPORATION, Tokyo (JP)

( * ) Notice: Subject to any disclaimer, the term of this patent is extended or adjusted under 35 U.S.C. 154(b) by 53 days.

(21) Appl. No.: 13/975,413

(22) Filed: Aug. 26, 2013

(65) Prior Publication Data

US 2014/0055783 A1 Feb. 27, 2014

(30) Foreign Application Priority Data

Aug. 27, 2012 (JP) ................................. 2012-186354
Jun. 4, 2013 (JP) ................................. 2013-117655

(51) Int. Cl.
*G01N 21/00* (2006.01)
*G01J 3/42* (2006.01)
(Continued)

(52) U.S. Cl.
CPC . *G01J 3/42* (2013.01); *G01N 21/33* (2013.01); *G01N 21/3563* (2013.01); *G01N 21/55* (2013.01); *G01N 2021/3568* (2013.01)

(58) Field of Classification Search
CPC ........... G01J 3/42; H01L 21/00; G01N 21/55; G01N 2021/3568
See application file for complete search history.

(56) References Cited

U.S. PATENT DOCUMENTS 8,680,509 B2 * 3/2014 Ooshika et al. ................. 257/22
2014/0166943 A1 * 6/2014 Ooshika et al. ............... 252/512

FOREIGN PATENT DOCUMENTS

JP 1-94247 A 4/1989
JP 7-63668 A 3/1995

OTHER PUBLICATIONS

Jiang, H., et al. "Determination of exciton transition energy and bowing parameter of AlGaN alloys in AlGaN/GaN heterostructu re by means of reflectance measurement." Journal of Applied Physics 89.2 (Year: 2001): 1046-1052.*

(Continued)

*Primary Examiner* — Michael A Lyons
*Assistant Examiner* — Shawn Decenzo
(74) *Attorney, Agent, or Firm* — Buchanan, Ingersoll & Rooney PC

(57) ABSTRACT

A method of analyzing a nitride semiconductor layer in which a mixing ratio at a ternary mixed-crystal nitride semiconductor layer can be analyzed non-destructively, simply, and precisely, even its surface is covered with a cap layer is provided. The nitride semiconductor layer having an AN layer or a BN layer with a thickness of 0.5 to 10 nm that is stacked on an $A_xB_{1-x}N$ layer (A and B: 13 group elements, $0 \leq x \leq 1$) is subjected to reflection spectroscopy to obtain a reflection spectrum of the $A_xB_{1-x}N$ layer. Let an energy value in a peak position of the reflection spectrum be a band gap energy $E_{gap}$, and let a band gap energy value of $A_xB_{1-x}N$ (x=1) be $E_A$ and a band gap energy value of $A_xB_{1-x}N$ (x=0) be $E_B$, x is calculated from Equation $E_{gap}=(1-x)E_B+xE_A-bx(1-x)$ (where b is bowing parameter corresponding to A and B).

4 Claims, 5 Drawing Sheets

(51) Int. Cl.
*G01N 21/33* (2006.01)
*G01N 21/3563* (2014.01)
*G01N 21/55* (2014.01)

(56) References Cited

OTHER PUBLICATIONS

Yun F. et al, J. Appl. Phys. 92, pp. 4837-4839(Year: 2002).*
Wetzel, C., et al. "Optical band gap in Ga 1-x In x N (0<< x<< 0.2) on GaN by photoreflection spectroscopy." Applied physics letters 73.14 (Year: 1998): 1994-1996.*
Moses, Poul Georg, et al. "Hybrid functional investigations of band gaps and band alignments for AlN, GaN, InN, and InGaN." The Journal of chemical physics 134.8 (Year: 2011): 084703.*
Katsuki Takeuchi et al., Optical properties of AlxGa1-xN alloy, Journal of Applied Physics, 107, 023306, 2010, pp. 1-11.
D. Brunner et al., Optical constants of epitaxial AlGaN films and their temperature dependence, J. Appl. Phys. 82 (10), Nov. 15, 1997, pp. 5090-5096.
Sadao Adachi, Optical dispersion relations for Si and Ge, J. Appl. Phys. 66 (7), Oct. 1, 1989, pp. 3224-3231.
D.F. Edwards, Silicon (Si) Revisited (1.4-6.0 eV), Handbook of Optical Constants of Solids III, 1998 pp. 531-536.
Jon Geist, Silicon (Si) Revisited (1.1-3.1 eV), Handbook of Optical Constants of Solids III, 1998, pp. 519-529.
Kiyoshi Yamamoto et al., Optical theory applied to infrared spectroscopy, Vibrational Spectroscopy 8, 1994, pp. 1-36.

* cited by examiner

METHOD OF ANALYZING NITRIDE SEMICONDUCTOR LAYER AND METHOD OF MANUFACTURING NITRIDE SEMICONDUCTOR SUBSTRATE USING THE ANALYSIS METHOD

BACKGROUND OF THE INVENTION

1. Field of the Invention

The present invention relates to an analysis method of finding a mixing ratio with respect to a nitride semiconductor used for an electronic device, a light emitting device, and a high frequency device, particularly with respect to a ternary mixed-crystal nitride semiconductor layer, and a method of manufacturing a nitride semiconductor substrate using the analysis method.

2. Description of the Related Art

In recent years, a nitride semiconductor substrate has been developed in which a nitride semiconductor layer of gallium nitride (GaN) suitable for a high withstand-voltage power device is deposited and formed on a substrate.

As an example of such, there may be mentioned a high electron mobility transistor (HEMT) with a structure where GaN layers as electron transit layers and $Al_xGa_{1-x}N$ single crystal layers ($0 \le x \le 1$) as electron supply layers are stacked one by one on a Si substrate through a buffer layer.

In a HEMT substrate, it is especially important to precisely control x in the $Al_xGa_{1-x}N$ single crystal layer ($0 \le x \le 1$) of the electron supply layer, i.e., a mixing ratio. As a method of measuring the mixing ratio of a mixed-crystal nitride semiconductor, the Rutherford backscattering method, the photo-luminescence method, etc. are known.

As an example of the method of measuring the mixing ratio by the photo-luminescence method, Japanese Patent Application Publication No. H1-94247 (Patent Literature 1) discloses a method in which excitation light by dye laser having optical energy higher than that of the band gap of the mixed crystal is applied to a sample surface to obtain a photo-luminescence spectrum generated from a sample, a penetration depth P of the excitation light inside a thin film sample is changed by changing an oscillation wavelength of the dye laser to obtain a photo-luminescence spectrum as a function of the penetration depth P, a band gap Eg is obtained as a function of a depth D from a combination of the photo-luminescence spectra, and the mixing ratio x by depth D is found from the band gap Eg.

Further, Japanese Patent Application Publication No. H7-63668 (Patent Literature 2) discloses that the sample surface irradiated with intensity-modulated excitation light is irradiated with probe light, and a reflection spectrum synchronized with the modulation is detected from the reflection light, so that a compound composition is found from energy at an absorption edge of the sample in which the energy is found from this reflection spectrum.

However, although the Rutherford backscattering method is excellent in measurement accuracy, an apparatus therefor is large in size and costly, and the measurement is carried out under vacuum, so that it requires time and effort for measurement per one sample. Therefore, it cannot be said that it is suitable for a simple and non-destructive measuring method to be used by incorporating itself into the manufacture process of the nitride semiconductor substrate especially.

Further, although the method by way of the photo-luminescence method described in Patent Literature 1 allows simple and non-destructive measurement, there is a possibility that it may be influenced by crystallinity, dislocation, etc., of a semiconductor layer of a measuring object, and it is hard to say that the stability and reliability of the measurement are fully secured. Furthermore, in the case where a film is formed on a surface of the semiconductor layer of the measuring object, the measurement is difficult because of the luminescence disturbance due to a quantum well structure.

Still further, Patent Literature 2 says that the technology described therein allows the composition of the compound semiconductor to be obtained easily and precisely compared with a fluorescent X-ray analysis. However, the modulation intensity of the reflection light also has a possibility that it may be influenced by crystallinity, dislocation, etc., of the semiconductor layer of the measuring object, and this technology does not fully secure the stability and reliability of the measurement.

SUMMARY OF THE INVENTION

The present invention arises in view of such problems in the conventional technologies, and aims at providing a method of analyzing a nitride semiconductor layer in which a mixing ratio at a ternary mixed-crystal nitride semiconductor layer can be analyzed non-destructively, simply, and precisely, even in the case where a surface of the nitride semiconductor layer is covered with a cap layer, and a method of manufacturing a nitride semiconductor substrate using the analysis method.

The method of analyzing the nitride semiconductor layer in accordance with the present invention is characterized by comprising a measurement step in which a nitride semiconductor layer having an AN layer or a BN layer with a thickness of 0.5 to 10 nm that is stacked on an $A_xB_{1-x}N$ layer (where A and B are 13 group elements, N is nitrogen, and $0 \le x \le 1$) is subjected to reflection spectroscopy to obtain a reflection spectrum of the above-mentioned $A_xB_{1-x}N$ layer, an analysis step of obtaining a band gap energy value $E_{gap}$ of the above-mentioned $A_xB_{1-x}N$ layer from the above-mentioned reflection spectrum, and a calculation step of calculating x from the above-mentioned band gap energy value $E_{gap}$, wherein let an energy value in a peak position of the above-mentioned reflection spectrum be $E_{gap}$ in the above-mentioned analysis step, and let a band gap energy value of $A_xB_{1-x}N$ (x=1) be $E_A$ and a band gap energy value of $A_xB_{1-x}N$ (x=0) be $E_B$ in the above-mentioned calculation step, x is calculated from Equation $E_{gap}=(1-x)E_B+xE_A-bx(1-x)$ (where b is bowing parameter corresponding to the above-mentioned A and B).

According to such a method, the AN mixing ratio x of the nitride semiconductor layer made of $A_xB_{1-x}N$ can be analyzed non-destructively, simply, for a short time, and precisely.

In the above-mentioned analysis method, instead of the energy value in the peak position of the above-mentioned reflection spectrum, the energy value at the frequency which gives an extreme value of differential by frequency of the above-mentioned reflection spectrum may be used as $E_{gap}$ used in the above-mentioned Equation.

According to this method, the analysis accuracy can be improved further.

Further, the method of manufacturing the nitride semiconductor substrate in accordance with the present invention is a method of manufacturing a nitride semiconductor substrate having a nitride semiconductor layer comprising at least one $A_xB_{1-x}N$ layer (where A and B are 13 group elements, N is nitrogen, and $0 \le x \le 1$), and characterized by including a step in which x of the above-mentioned $A_xB_{1-x}N$ layer is calculated by the above-mentioned analysis method to change manufacture conditions based on x.

By applying the above-mentioned analysis method to the manufacture process of the nitride semiconductor substrate, it is possible to simply manufacture the nitride semiconductor substrate whose mixing ratio is controlled precisely.

According to the method of analyzing the nitride semiconductor layer in accordance with the present invention, the AN mixing ratio x of $A_xB_{1-x}N$ of the ternary mixed-crystal nitride semiconductor can be analyzed non-destructively, simply, and precisely at room temperature and under atmospheric conditions, even in the case where its surface is covered with the cap layer.

Further, according to the manufacture method using the analysis method in accordance with the present invention, it is possible to provide the nitride semiconductor substrate whose mixing ratio is precisely controlled by a simple method.

DESCRIPTION OF THE PREFERRED EMBODIMENTS

Figure 1:
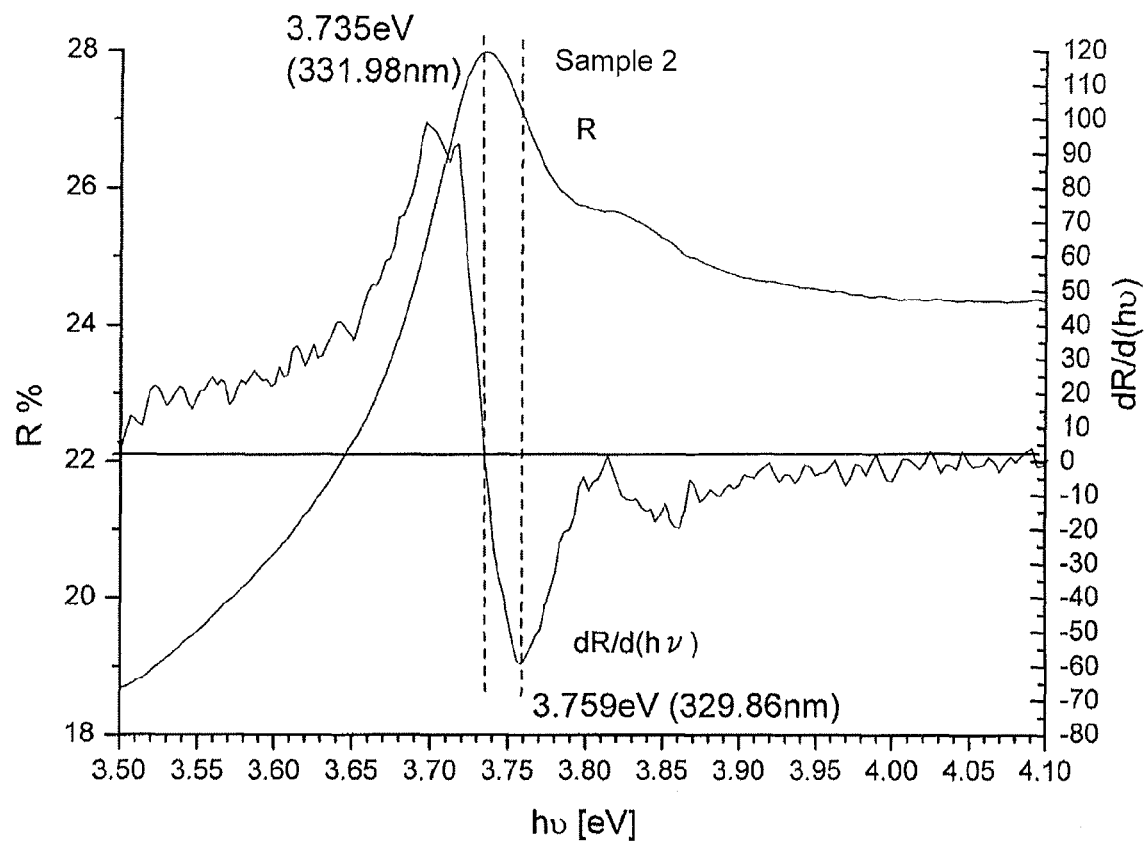
FIG. 1 is a graph showing an ultra-violet reflection spectrum of Sample 2 in Example and differential values by frequency of the reflection spectrum.

Hereinafter, the preferred embodiments of the present invention will be described in more detail.

A method of analyzing a nitride semiconductor layer in accordance with the present invention includes a measurement step in which a nitride semiconductor layer having an AN layer or a BN layer with a thickness of 0.5 to 10 nm that is stacked on an $A_xB_{1-x}N$ layer (where A and B are 13 group elements, N is nitrogen, and $0 \leq x \leq 1$) is subjected to reflection spectroscopy to obtain a reflection spectrum of the above-mentioned $A_xB_{1-x}N$ layer, an analysis step of obtaining a band gap energy value $E_{gap}$ of the above-mentioned $A_xB_{1-x}N$ layer from the above-mentioned reflection spectrum, and a calculation step of calculating x from the above-mentioned band gap energy value $E_{gap}$.

Further, let an energy value in a peak position of the above-mentioned reflection spectrum be $E_{gap}$ in the above-mentioned analysis step, and let a band gap energy value of $A_xB_{1-x}N$ (x=1) be $E_A$ and a band gap energy value of $A_xB_{1-x}N$ (x=0) be $E_B$ in the above-mentioned calculation step, x is calculated from Equation $E_{gap}=(1-x)E_B+xE_A-bx(1-x)$ (where b is bowing parameter corresponding to A and B above).

$A_xB_{1-x}N$ to be analyzed is a ternary mixed-crystal nitride semiconductor, and A and B are 13 group elements. In particular, there may be mentioned $In_xGa_{1-x}N$, $Al_xIn_{1-x}N$, $Al_xGa_{1-x}N$, etc., where x of $A_xB_{1-x}N$ is a mixing ratio of AN in the nitride semiconductor of the ternary mixed-crystal, and between 0 and 1 (inclusive).

It should be noted that the analysis method in accordance with the present invention can be applied in the case where carbon, boron, phosphorus, silicon, etc. are included as impurities or dopants.

The present invention is a method for simply and precisely analyzing an AN mixing ratio x of $A_xB_{1-x}N$ ($0 \leq x \leq 1$) which is a ternary mixed-crystal nitride semiconductor and provides a method to be performed using reflection spectroscopy.

The analysis method in accordance with the present invention makes it possible to evaluate the mixing ratio by a simple technique in which the peak position of the reflection spectrum is detected based on the finding that the peak frequency of the reflection spectrum is in agreement with a frequency of a singular point of a dielectric constant according to calculation simulation in various conditions and actual measurements.

In other words, the method in accordance with the present invention is that based on the finding an electronic state relationship between reflectivity and a dielectric constant, the reflection spectroscopy is carried out near an absorption edge of $A_xB_{1-x}N$ (200 to 360 nm for AlGaN), and a singular point of a dielectric function is estimated from the form of the reflection spectrum to find the AN mixing ratio x from the band gap energy.

Further, for example, a nitride semiconductor substrate usually has a hetero-epitaxial structure of "$A_xB_{1-x}N$/BN/multi-buffer/substrate", and is shipped as a product in which a cap layer made of very thin AN or BN with a thickness of 0.5 to 10 nm is formed as a film on a $A_xB_{1-x}N$ surface for surface protection. For example, in the case where the above-mentioned $A_xB_{1-x}N$ layer is an $Al_xGa_{1-x}N$ layer, a GaN layer is usually formed as the cap layer.

As such, in the case where the $A_xB_{1-x}N$ layer is covered with the cap layer, light-emission based on a quantum well structure of the very thin cap layer takes place as described above in a photo-luminescence method. Further, light emission of $A_xB_{1-x}N$ exciton is blocked by the light emission from the cap layer, and cannot be measured in practice.

On the other hand, according to the reflection spectroscopy, the reflection spectrum can be measured, substantially without being influenced by the cap layer. Thus, according to the method in accordance with the present invention, as for the nitride semiconductor layer having the AN layer or BN layer stacked thereon with a thickness of 0.5 to 10 nm, it is possible to find the mixing ratio of the nitride semiconductor layer simply, precisely, and non-destructively at room temperature and under atmospheric conditions.

A thickness of the AN layer or BN layer (cap layer) stacked on the above-mentioned $A_xB_{1-x}N$ layer is 0.5 to 10 nm, and preferably 2 to 5 nm.

The thickness of the above-mentioned cap layer is preferably thin in the range in which the effect of protecting the product is not spoiled. However, if it is too thin, variations in layer thickness become relatively large, and there is a possibility of the influence on various device properties. Further, if it exceeds 10 nm, there is a possibility of the influence on the reflection spectrum, this is not preferred.

Further, when considering the above-mentioned analysis method, it is confirmed that a frequency which gives an extreme of the differential function by frequency is a little closer to the singular point than the frequency peak position of the reflectivity. Thus, in the case of finding a mixing ratio more precisely, it is preferable that the frequency which gives the extreme of the differential function by frequency of the reflection spectrum measured at a high S/N ratio is set as the singular point.

Now, a method of calculating the extreme by frequency of the differential function and carried out for $Al_{1-x}Ga_xN$ as a typical example of $A_xB_{1-x}N$ will be described. In particular, the calculation is carried out for the nitride semiconductor substrate comprising multilayer film where GaN and $Al_xGa_{1-x}N$ are deposited one by one on a Si substrate through a multi-buffer layer.

An optical characteristic matrix (2 rows×2 columns) reflecting a complex dielectric function (dispersion of complex dielectric constant) in an ultra-violet range is applied to each layer which constitutes the above-mentioned nitride substrate, and the property of the above-mentioned whole multilayer film is expressed by a product of the characteristic matrices, and the reflectivity is found using the components of the characteristic matrix.

A model function disclosed in K. Takeuchi et al., J. Appl. Phys., 107, 23306 (2010) is used for the complex dielectric function $\in(\omega)$ of and GaN with respect to a frequency $\omega$. Further, a function disclosed in D. Brunner et al., J. Appl. Phys., 82, 5090 (1997) is used for the dielectric function of AlN. A function described in the papers of S. Adachi, J. Appl. Phys., 66, 3224 (1989) and D. F. Edwards, "Silicon (Si)" Handbook of Optical Constants of Solids III, E. D. Palik, ed., Academic Press, (1998) is used for the dielectric function of Si of the substrate. Furthermore, behavior of incident light at each wavelength is calculated by a method for using a matrix which describes a light transparency and reflection property of the multilayer film (see K. Yamamoto et al., Vibrational Spectroscopy 8, 1, (1994)). It should be noted that actual numerical computation is performed using technical calculation and document software MathCad11.

In addition, since the reflection peak wavelength does not always correspond to the transverse wave (resonance) frequencies of the exciton of $Al_xGa_{1-x}N$ and GaN, it is necessary to find a resonance frequency of $Al_xGa_{1-x}N$ from the reflection spectrum by a certain method in order to find an AlN mixing ratio x of $Al_xGa_{1-x}N$. As the simplest way, it is possible to find the resonance frequency from the maximum and the minimum of the first order differential $dR(\omega)/d\omega$, which is the reflection spectrum $R(\omega)$ differentiated by the incident light frequency $\omega$. Since $dR(\omega)/d\omega$ includes information about the maximum and minimum of a real part $\in 1(\omega)$ and imaginary part $\in 2(\omega)$ of the dielectric function, a resonance (transverse wave) frequency becomes a frequency at which the imaginary part $\in 2(\omega)$ is the extreme.

Table 1 shows values of the resonance wavelengths respectively found from setting values of the resonance wavelengths of the excitons of AlGaN and GaN, the imaginary part maximum $Im\in(\omega)$ of the dielectric constant considered to correspond thereto, $dR(\omega)/d\omega$ extreme, and the reflection peak $R(\omega)$, with respect to the nitride semiconductor substrates of Samples 1 and 2 in the preferred embodiment to be set forth later and one in which no cap layer is included unlike in Sample 4.

TABLE 1

| | Resonance Wavelength (nm) | Sample 1 GaN | Sample 2 $Al_{0.15}Ga_{1-0.15}N$ | One having no cap layer unlike Sample 4 $Al_{0.26}Ga_{1-0.26}N$ |
|---|---|---|---|---|
| AlGaN layer | Setting Wavelength | | 328.60 | 307.42 |
| | $Im \epsilon (\omega)$ | | 330.63 | 309.95 |
| | $dR(\omega)/d\omega$ | | 327.99 | 309.95 |
| | $R(\omega)$ | | 333.25 | 310.93 |
| GaN layer | Setting Wavelength | 359.37 | 359.37 | 359.37 |
| | $Im \epsilon (\omega)$ | 361.46 | 361.46 | 361.46 |
| | $dR(\omega)/d\omega$ | 361.46 | 361.46 | 359.37 |
| | $R(\omega)$ | 363.58 | 362.54 | 361.46 |

As shown in Table 1, it can be seen that the value of the resonance wavelength found from the first order differential $dR(\omega)/d\omega$ of the reflectivity is substantially equal to the value calculated from the maximum of the imaginary part $Im\in(\omega)$ of the dielectric constant which is usual calculation of a resonance frequency in the case where the dielectric function is given, and it is closer to the setting value than the value calculated from the reflection peak $R(\omega)$.

From this calculation result, it can be said that using the maximum and minimum wavelengths of the first order differential $dR(\omega)/d\omega$ of the reflectivity is preferable to using a reflectivity peak wavelength as the resonance wavelength obtained from the reflection spectrum. However, since an actual spectrum contains noises, it is preferable to improve a S/N ratio as much as possible, and to perform smoothing if necessary.

Therefore, in the analysis step of the above-mentioned method, instead of the energy value in the peak position of the reflection spectrum of the $A_xB_{1-x}N$ layer, the energy value at the frequency which gives an extreme value of differential by frequency of the above-mentioned reflection spectrum is used as the band gap energy value $E_{gap}$, to thereby find the mixing ratio more precisely.

According to the method in accordance with the present invention, in the measurement step of obtaining the reflection spectrum of the $A_xB_{1-x}N$ layer by reflection spectroscopy, in particular, the reflection spectrum can be obtained using the method (wavelength dispersion system of incident light) of measuring reflection light intensity while scanning the incident light wavelength. Alternatively, as a simpler system, the reflection spectrum can also be obtained by the method (wavelength dispersion system of reflection light) of allowing incidence of continuous spectrum light, and dispersing the reflected light with a spectroscope.

Further, from the thus obtained reflection spectrum, the band gap energy value $E_{gap}$ of $A_xB_{1-x}N$ is obtained in the analysis step. In the following calculation step, this band gap energy value $E_{gap}$ (unit:eV) is used as a peak position of the reflection spectrum or the energy at the frequency which gives the extreme value of differential by frequency of the above-mentioned reflection spectrum. Furthermore, let the band gap energy value of $Al_xB_{1-x}N$ (x=1) be $E_A$ and let the band gap energy value of $A_xB_{1-x}N$ (x=0) be $E_B$, the AN mixing ratio x is calculated from Equation $E_{gap}=(1-x)E_B+xE_A-bx(1-x)$ (where b is bowing parameter corresponding to A and B, above).

For example, in the case where the nitride semiconductor layer to be analyzed is an AlGaN layer, the above-mentioned Equation is $E_{gap}=(1-x)E_{GaN}+xE_{AlN}-bx(1-x)$, then a band gap energy of GaN is $E_{GaN}=3.4$ to $3.5$ eV, a band gap energy of AlN is $E_{AlN}=6.1$ to $6.2$ eV, and the bowing parameter is $b=0.85$. In addition, $E_{GaN}=3.42$ eV and $E_{AlN}=6.2$ eV are used in actual calculation.

Using these Equations, in the nitride semiconductor substrate having a stacked configuration of "GaN cap layer/AlGaN/GaN/buffer/substrate" where hetero-epitaxial growth is carried out by the MOCVD method etc., it is possible to readily find the AlN mixing ratio of the AlGaN layer, even if a thickness of the AlGaN layer is around 10 to 40 nm.

Figure 2:
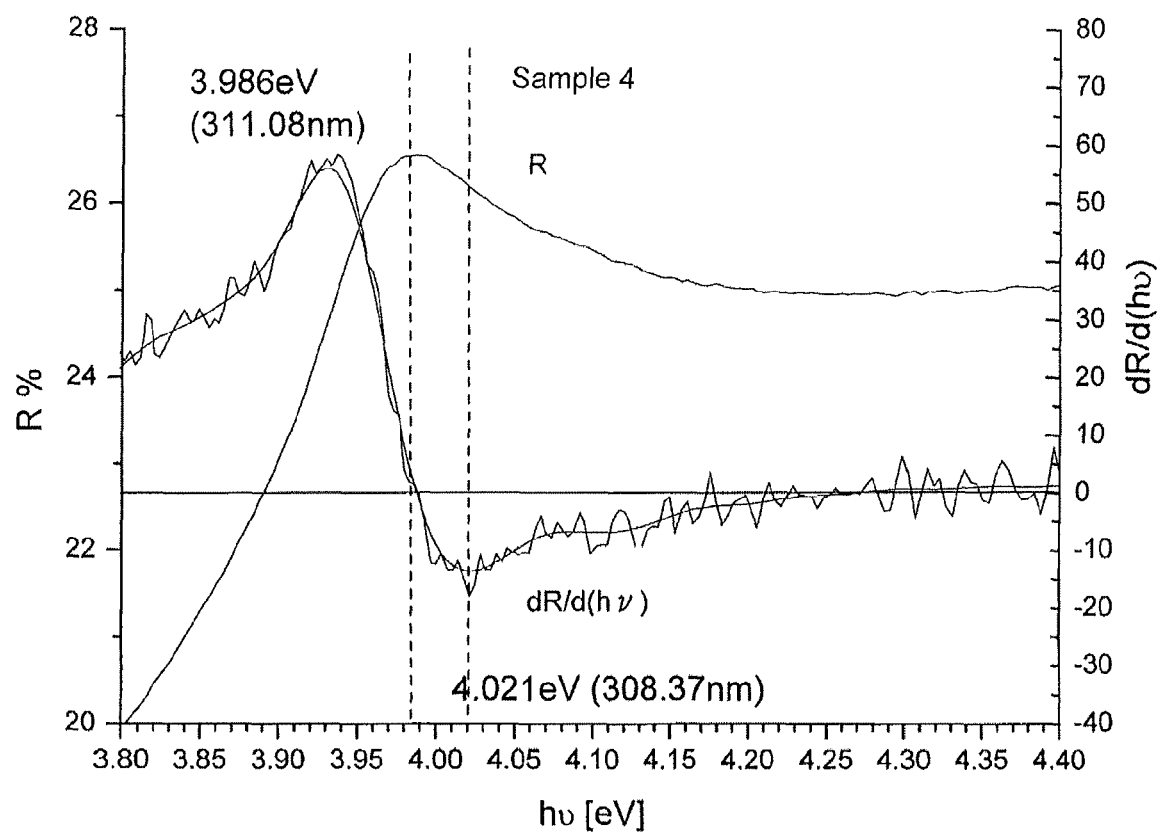
FIG. 2 is a graph showing an ultra-violet reflection spectrum of Sample 4 in Example and differential values by frequency of the reflection spectrum.

Further, FIGS. 1 and 2 show graphs of the reflection spectra and the differential values by frequency of the reflection spectra respectively for Samples 2 and 4 in the preferred embodiment to be set forth later. A horizontal axis represents photon energy hv(eV), a left vertical axis represents the reflectivity, and a right vertical axis represents the reflectivity differential.

As shown in FIGS. 1 and 2, a difference between the reflection peak position of AlGaN and the differential extreme point of either Sample is 35 meV or less. Whichever singular point is used, there is no large difference in the calculation value of the AlN mixing ratio. Thus, it is confirmed that Sample 2 results in x=0.15 and Sample 4 results in x=0.26 as expected in a film forming process.

Further, according to the present invention, a manufacture method can be provided, comprising the step in which when manufacturing the nitride semiconductor substrate having the nitride semiconductor layer comprising at least one $A_xB_{1-x}N$ layer, x of the above-mentioned $A_xB_{1-x}N$ layer is calculated by the above-mentioned analysis method to change manufacture conditions based on x.

Thus, the above-mentioned analysis method can be incorporated into and applied to the manufacture process as one step, to thereby simplify the manufacture of the nitride semiconductor substrate whose mixing ratio is precisely controlled.

In addition, the present invention is not limited to the so-called single hetero-epitaxial structure, such as the above-mentioned "GaN cap layer/AlGaN/GaN/buffer/substrate", but may be applied also to the nitride semiconductor substrate having a so-called double hetero-epitaxial structure and provided with an arrangement where GaN layers have two "AlGaN/GaN" interfaces, like "GaN cap layer/AlGaN/GaN/AlGaN/GaN/buffer/substrate", i.e. "$Al_xGa_{1-x}N/GaN/Al_yGa_{1-y}N$". In this case, according to the analysis method in accordance with the present invention, it is possible to find the AlN mixing ratios x and y in two AlGaN layers respectively.

Further, using an energy value E obtained by fitting (applying) the Lorenz type function to the reflection peak of the $A_xB_{1-x}N$ (for example $Al_xGa_{1-x}N$) layer, x can be found from a formula expressed as $E=(1-x)E_B+xE_A-bx(1-x)$ (where $E_{A'}$ is the exciton energy of AN and $E_{B'}$ is the exciton energy of BN). According to this method, depending on conditions, it is possible to calculate the value x more precisely.

In addition, the formula shown below is used for the Lorenz type function.

$$R(v) = R_0 + \sum_{j=1}^{3} R_j \text{Re}\left[\frac{hv_j - hv + i\Gamma_j}{\Gamma_j^2 + (hv - hv_j)^2}\exp(i\Theta_j)\right]$$

where v is a frequency, $R_0$ is a background reflectivity, "Re[ ]" indicates a real part of a complex number within [ ], and j's in j=1, 2, 3 respectively correspond to free excitons A, B, and C. Further, for each j, $R_j$ represents amplitude, $hv_j$ represents exciton energy, $\Gamma_j$ represents a broadening parameter, $\Theta_j$ represents a phase, and $i^2=-1$.

EXAMPLE

Hereinafter, the present invention will be described more particularly with reference to Examples, however the present invention is not limited to the following Examples.

Example 1

Nitride semiconductor substrate Samples 1 to 5 having stacked configurations shown in Table 2 below were prepared. Each Sample was subjected to ultra-violet reflection spectroscopy of a wavelength dispersion system of incident light to obtain a reflection spectrum.

It should be noted that, in Table 1, a (111) Si substrate was heavily doped with Sb (to have a resistivity of 10 to 20 mΩ·cm). Further, the multi-layer formed therein 85 sets of (AlN (5 nm)/GaN (20 nm)) layers, and the buffer layer formed therein an AlGaN (100 nm)/AlN (100 nm) layer.

TABLE 2

| Sample 1 | Sample 2 | Sample 3 | Sample 4 | Sample 5 |
|---|---|---|---|---|
|  |  | GaN Cap layer (2 nm) | GaN Cap layer (2 nm) | GaN Cap layer (2 nm) |
|  | $Al_{0.15}Ga_{1-0.15}N$ (Approx. 40 nm) | $Al_{0.15}Ga_{1-0.15}N$ (Approx. 40 nm) | $Al_{0.26}Ga_{1-0.26}N$ (Approx. 20 nm) | $Al_{0.26}Ga_{1-0.26}N$ (Approx. 20 nm) |
| GaN (1.5 μm) | GaN (1.5 μm) | GaN (1.5 μm) | GaN (1.5 μm) | GaN (1.5 μm) |
| Multi-buffer (2.5 μm) | Multi-buffer (2.5 μm) | Multi-buffer (2.5 μm) | Multi-buffer (2.5 μm) | Multi-buffer (2.5 μm) |
| Si substrate | Si substrate | Si substrate | Si substrate (Warpage 20 μm) | Si substrate (Warpage 450 μm) |

Example 2

The above-mentioned Samples 1 to 5 were subjected to the ultra-violet reflection spectroscopy of a wavelength dispersion system of reflection light to obtain a reflection spectrum.

Figure 3:
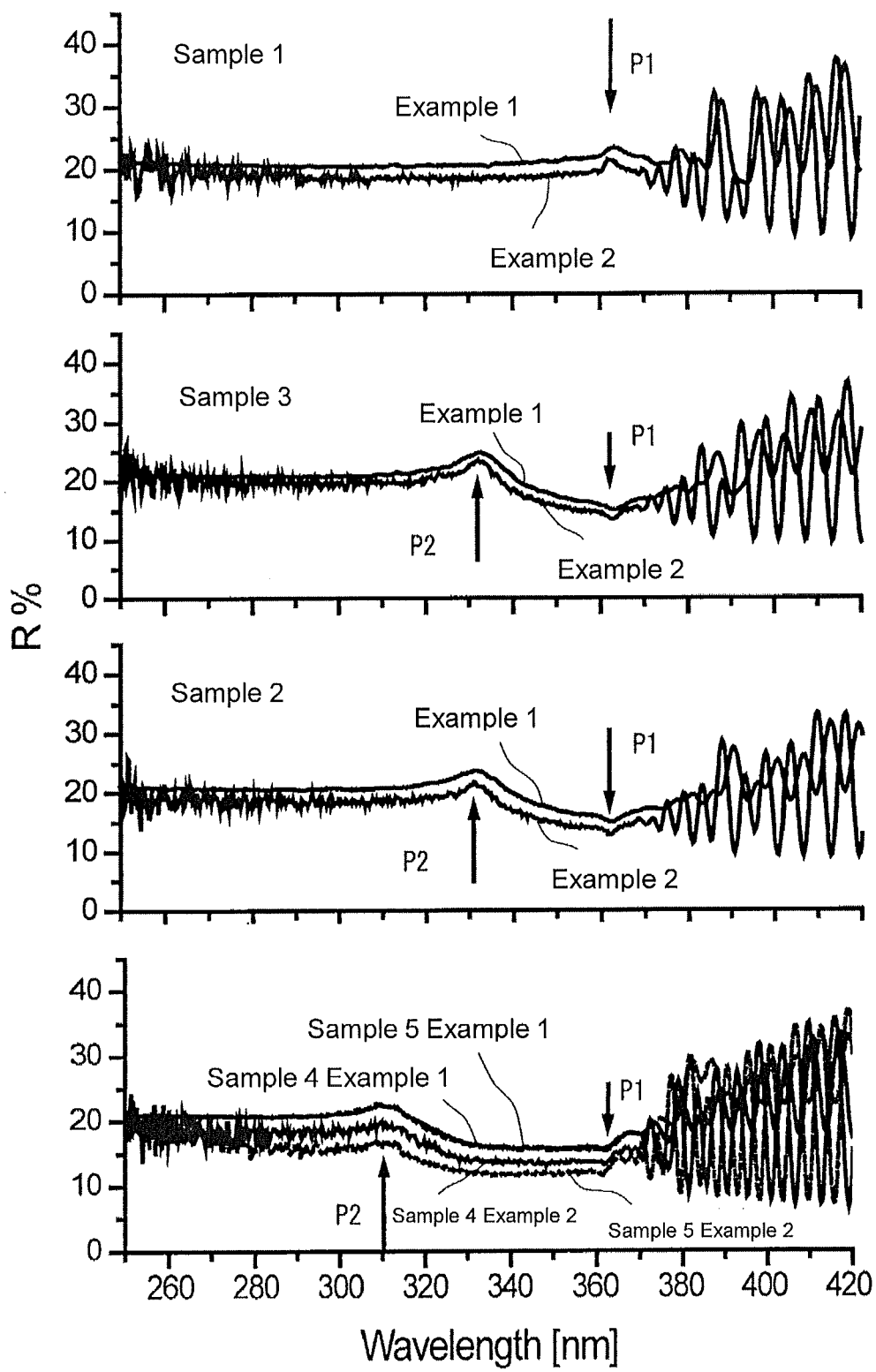
FIG. 3 shows ultra-violet reflection spectra of Samples 1 to 5 measured in Examples 1 and 2.

The reflection spectra of the samples 1 to 5 measured in Examples 1 and 2 are shown in FIG. 3.

As can be seen from FIG. 3, since Sample 1 did not have the AlGaN layer, only a peak P1 with a wavelength of 362 nm corresponding to the singular point of GaN was observed. On the longer wavelength side than that of this peak, interference fringes appeared. Either of measuring methods of the wavelength dispersion system of incident light (Example 1) and the wavelength dispersion system of reflection light (Example 2) resulted in the same peak wavelength of GaN.

Sample 2 formed $A_{0.15}Ga_{1-0.15}N$ (AlN mixing ratio 15%) as a film on the GaN layer of Sample 1. Sample 3 further formed a GaN cap layer with a thickness of 2 nm as a film on the $Al_{0.15}Ga_{1-0.15}N$ layer of Sample 2.

Also for Samples 2 and 3, as shown in FIG. 3, similar reflection spectrum peaks were obtained by either of the measuring methods of the wavelength dispersion system of incident light (Example 1) and the wavelength dispersion system of reflection light (Example 2). Sample 3 was not influenced by the GaN cap layer and resulted in a similar reflection spectrum to that of Sample 2. Further, unlike Sample 1, the peak P1 with a wavelength of 362 nm corresponding to the singular point of GaN downwardly projected. Furthermore, a peak P2 corresponding to the singular point of AlGaN was observed at a wavelength of 330 nm on the shorter wavelength side.

Samples 4 and 5 each formed an $Al_{0.26}Ga_{1-0.26}N$ (AlN mixing ratio 26%) layer as a film on the Lop of GaN layer of Sample 1 and further formed a GaN cap layer with a thickness of 2 nm as a film on the $Al_{0.26}Ga_{1-0.26}N$ layer. In addition, a concave warpage in the center of the substrate (wafer with a diameter of 150 mm) of Sample 4 was 20 μm and that of Sample 5 was 450 μm.

Also as for Samples 4 and 5, as shown in FIG. 3, similar reflection spectrum peaks were obtained by either of the measuring methods of the wavelength dispersion system of incident light (Example 1) and the wavelength dispersion system of reflection light (Example 2). Further, the influence of the GaN cap layer was not observed.

With increasing AlN mixing ratio, the peak P2 corresponding to the singular point of AlGaN was observed at a wavelength of 310 nm on the shorter wavelength side according to Equation $E_{gap}=(1-x)E_{Ga}+xE_{Al}-bx(1-x)$. Further, the influence of the warpage of the substrate was not seen, either.

In addition, for the above-mentioned Samples 1 to 5, the calculation simulation was carried out using the above-mentioned model dielectric function theory to find an ultra-violet reflection spectrum. When this reflection spectrum was compared with the reflection spectrum of the actual measurements in Examples 1 and 2, it was confirmed that both were substantially qualitatively in agreement with each other.

Comparative Example 1

Figure 4:
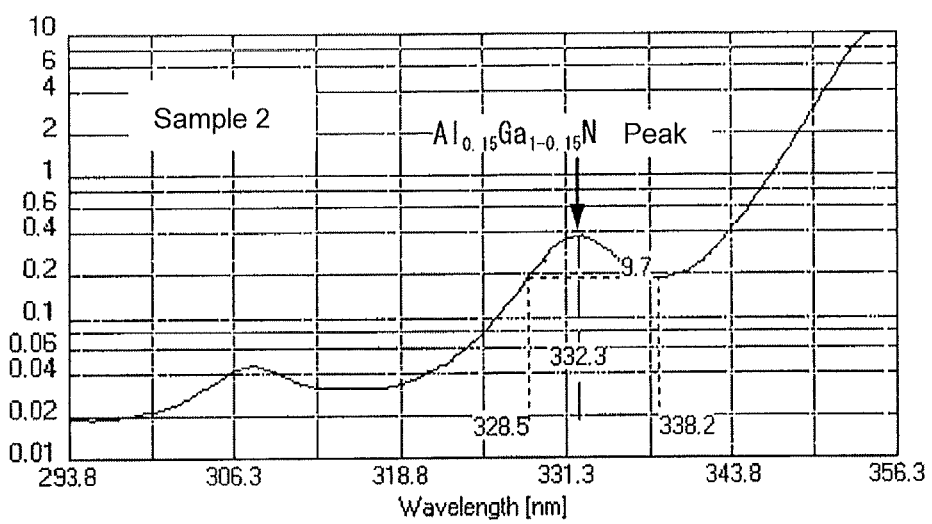
FIG. 4 shows fluorescence spectra of Samples 2 and 3 measured in Comparative Example 1 by a photo-luminescence method (266 nm excitation).
Figure 4:
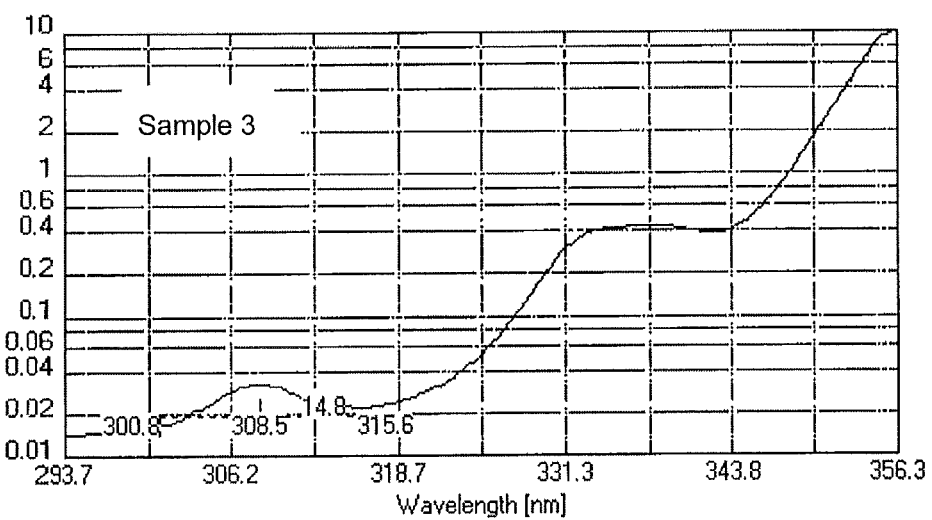

As for Samples 2 and 3, fluorescence spectra measured by the photo-luminescence method (266 nm excitation) are shown in FIG. 4.

As can be seen from FIG. 4, the luminescence peak of AlGaN was not detected, since its peak was overlapped with the luminescence peak of the GaN cap layer in the case where the GaN cap layer was formed (Sample 3).

Example 3

As with the similar stacked configuration to that in Sample 2, 19 types of samples each having formed therein the AlGaN layer as a film and having a different mixing ratio were prepared. Each Sample was subjected to the wavelength dispersion system of reflection light (as in Example 2) to measure an ultra-violet reflection spectrum and also measured by the photo-luminescence method. As for the measured spectrum peaks of AlGaN, FIG. 5 shows a correlation between them graphically.

Figure 5:
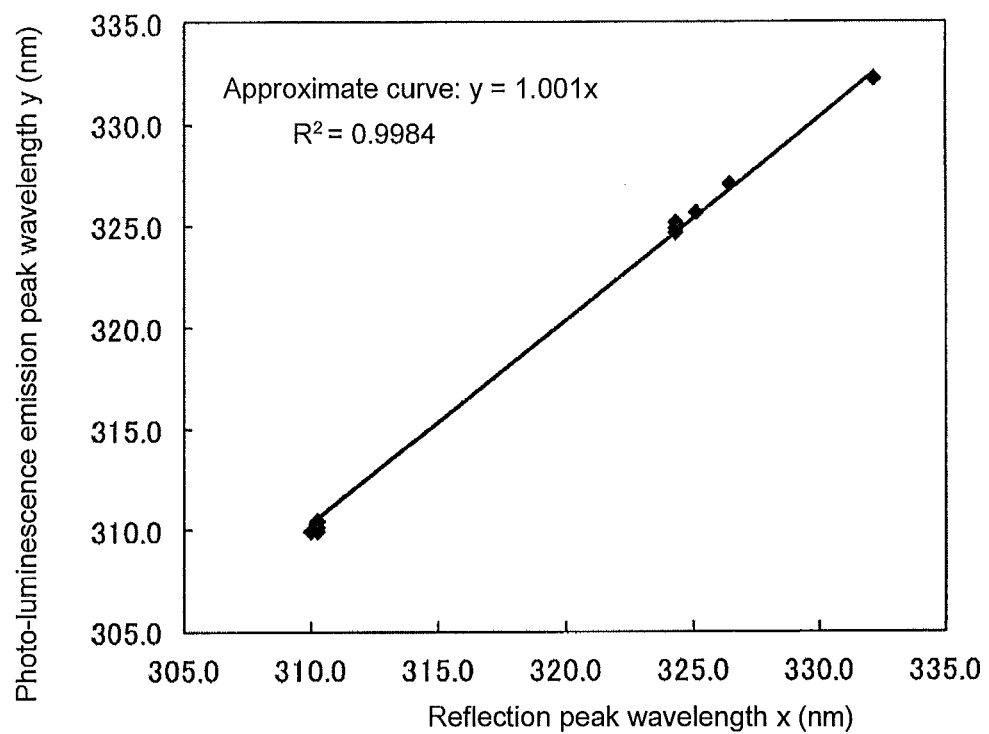
FIG. 5 is a graph showing a wavelength correlation between an ultra-violet reflection peak of $Al_xGa_{1-x}N$ and a photo-luminescence emission peak.

As shown in FIG. 5, it was confirmed that the wavelengths of the reflection peak of AlGaN and a photo-luminescence emission peak, corresponding to the mixing ratio, had a linear correlation over a wide range.

What is claimed is:

1. A method of analyzing a nitride semiconductor layer, comprising a measurement step in which a nitride semiconductor layer having an AN layer or a BN layer with a thickness of 0.5 to 10 nm that is stacked on an $A_xB_{1-x}N$ layer (where A and B are 13 group elements, N is nitrogen, and $0 \leq x \leq 1$) is subjected to reflection spectroscopy to obtain a reflection spectrum of said $A_xB_{1-x}N$ layer, an analysis step of obtaining a band gap energy value $E_{gap}$ of said $A_xB_{1-x}N$ layer from said reflection spectrum, and a calculation step of calculating x from said band gap energy value $E_{gap}$, wherein let an energy value in a peak position of said reflection spectrum be $E_{gap}$ in said analysis step, and let a band gap energy value of $A_xB_{1-x}N$ (x=1) be $E_A$ and a band gap energy value of $A_xB_{1-x}N$ (x=0) be $E_B$ in said calculation step, x is calculated from Equation $E_{gap}=(1-x)E_B xE_A-bx(1-x)$ (where b is bowing parameter corresponding to said A and B).

2. A method of manufacturing a nitride semiconductor substrate having a nitride semiconductor layer comprising at least one $A_xB_{1-x}N$ layer (where A and B are 13 group elements, N is nitrogen, and $0 \leq x \leq 1$), the method including a step in which x of said $A_xB_{1-x}N$ layer is calculated by the analysis method as claimed in claim 1 to change manufacture conditions based on x.

3. A method of analyzing a nitride semiconductor layer, comprising a measurement step in which a nitride semiconductor layer having an AN layer or a BN layer with a thickness of 0.5 to 10 nm that is stacked on an $A_xB_{1-x}N$ layer (where A and B are 13 group elements, N is nitrogen, and $0 \leq x \leq 1$) is subjected to reflection spectroscopy to obtain a reflection spectrum of said $A_xB_{1-x}N$ layer, an analysis step of obtaining a band gap energy value $E_{gap}$ of said $A_xB_{1-x}N$ layer from said reflection spectrum, and a calculation step of calculating x from said band gap energy value $E_{gap}$, wherein let an energy value at a frequency which gives an extreme value of differential by frequency of said reflection spectrum be $E_{gap}$ in said analysis step, and let a band gap energy value of $A_xB_{1-x}N$ (x=1) be $E_A$ and a band gap energy value of $A_xB_{1-x}N$ (x=0) be $E_B$ in said calculation step, x is calculated from Equation $E_{gap}=(1-x)E_B xE_A-bx(1-x)$ (where b is bowing parameter corresponding to said A and B).

4. A method of manufacturing a nitride semiconductor substrate having a nitride semiconductor layer comprising at least one $A_xB_{1-x}N$ layer (where A and B are 13 group elements, N is nitrogen, and $0 \leq x \leq 1$), the method including a step in which x of said $A_xB_{1-x}N$ layer is calculated by the analysis method as claimed in claim 3 to change manufacture conditions based on x.

* * * * *